(12) United States Patent
Hansma et al.

(10) Patent No.: US 9,983,107 B2
(45) Date of Patent: May 29, 2018

(54) SELF-ALIGNING PROBES AND RELATED DEVICES

(71) Applicant: The Regents of the University of California, Oakland, CA (US)

(72) Inventors: Paul K. Hansma, Goleta, CA (US); Connor Randall, Santa Barbara, CA (US); Daniel Bridges, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 43 days.

(21) Appl. No.: 14/392,010

(22) PCT Filed: Jul. 22, 2013

(86) PCT No.: PCT/US2013/000169
§ 371 (c)(1),
(2) Date: Jan. 20, 2015

(87) PCT Pub. No.: WO2014/018088
PCT Pub. Date: Jan. 30, 2014

(65) Prior Publication Data
US 2015/0323436 A1    Nov. 12, 2015

Related U.S. Application Data

(60) Provisional application No. 61/741,722, filed on Jul. 25, 2012.

(51) Int. Cl.
| | |
|---|---|
| *G01N 3/40* | (2006.01) |
| *G01N 3/04* | (2006.01) |
| *G01N 3/42* | (2006.01) |
| *A61B 5/00* | (2006.01) |

(52) U.S. Cl.
CPC ............ *G01N 3/40* (2013.01); *A61B 5/0053* (2013.01); *A61B 5/4504* (2013.01); *G01N 3/04* (2013.01); *G01N 3/42* (2013.01)

(58) Field of Classification Search
CPC ... G01N 3/42; G01N 3/40; G01N 3/04; A61B 5/103; A61B 5/0053; A61B 5/4504
USPC ...................................................... 73/12.09
See application file for complete search history.

(56) References Cited

U.S. PATENT DOCUMENTS

| | | | | |
|---|---|---|---|---|
| 4,530,160 A | * | 7/1985 | Feichtinger | G01B 5/012 33/559 |
| 4,752,166 A | * | 6/1988 | Lehmkuhl | G01B 5/012 33/504 |
| 4,778,313 A | * | 10/1988 | Lehmkuhl | B23B 29/03457 29/56.5 |

(Continued)

FOREIGN PATENT DOCUMENTS

WO    WO/2012/015592    4/2012

*Primary Examiner* — Natalie Huls
*Assistant Examiner* — Monica S Young
(74) *Attorney, Agent, or Firm* — Jeffrey A. McKinney; McKinney Law Group APC

(57) ABSTRACT

The field of the invention generally relates to probes, related devices and methods for measuring material properties. In an embodiment, the present invention provides a test probe for use in a reference point indentation device. The test probe has an end proximal to a tip and an end distal to the tip. The distal end of the test probe has a self-centering mate comprising a countersink of about 90 degrees to about 100 degrees to a depth of between 0.010 in. and 0.035 in.

10 Claims, 9 Drawing Sheets

(56) References Cited

U.S. PATENT DOCUMENTS

| | | | | |
|---|---|---|---|---|
| 5,365,673 | A | * | 11/1994 | Haimer .................. G01B 5/012 33/503 |
| 5,503,162 | A | * | 4/1996 | Athanasiou .......... A61B 5/0053 600/587 |
| 6,068,604 | A | * | 5/2000 | Krause .................... G01N 3/405 600/587 |
| 2007/0276292 | A1 | * | 11/2007 | Hansma ............... A61B 5/4504 600/587 |
| 2009/0093692 | A1 | * | 4/2009 | Hansma ................. A61B 5/103 600/306 |
| 2012/0046570 | A1 | * | 2/2012 | Villegas ............... A61B 5/0059 600/547 |

* cited by examiner 901　　　　　　　　903　　　　　　　　905

US 9,983,107 B2

SELF-ALIGNING PROBES AND RELATED DEVICES

This Application is a national phase application being filed under 37 CFR 371based on International application No. PCT/US2013/000169 having an International filing date of Jul. 22, 2013, which claims priority to U.S. Provisional Patent Application No. 61/741,722 filed on Jul. 25, 2012. Priority to the provisional patent application is claimed pursuant to 35 U.S.C. § 119. The above-noted patent applications are incorporated by reference as if set forth fully herein.

STATEMENT REGARDING FEDERALLY SPONSORED RESEARCH OR DEVELOPMENT

This invention was made with Government support under Grant No. RO1 GM065354, awarded by the National Institutes of Health. The Government has certain rights to this invention.

FIELD OF THE INVENTION

The field of the invention generally relates to probes, related devices and methods for measuring material properties.

BACKGROUND OF THE INVENTION

Various devices have been proposed to measure material properties. For instance, WO 2012/015592 reports a probe-based device that performs reference point indentation without a reference probe. The indentation distance is measured relative to the instrument which remains substantially stationary during the impact process, which occurs on the order of one millisecond. In one embodiment, an impact motion with a peak force of order 40N creates an indentation in bone with a depth of approximately 150 µm during which the instrument case moves less than 1 µm. Thus the error in measuring indentation depth due to the motion of the case is less than 1%, making a reference probe unnecessary.

Despite the various proposed devices, a need still exists in the art for novel material measuring probes, devices and methods.

SUMMARY OF THE INVENTION

The field of the invention generally relates to probes, related devices and methods for measuring material properties.

In an embodiment, the present invention provides a test probe for use in a reference point indentation device. The test probe has an end proximal to a tip and an end distal to the tip. The distal end of the test probe has a self-centering mate comprising a countersink of about 90 degrees to about 100 degrees to a depth of between 0.010 in. and 0.035 in.

In another embodiment, the present invention provides a probe mating chuck system for use in a reference point indentation device. The system comprises a test probe and a magnetic chuck. The test probe has an end proximal to a tip and an end distal to the tip. The distal end of the test probe has a self-centering mate comprising a countersink of about 90 degrees to about 100 degrees to a depth of between 0.010 in. and 0.035 in. The self-centering mate is mated to a magnetic chuck comprising an alignment ball, a ring magnet and an impact transfer shaft.

In another embodiment, the present invention provides a method of measuring a property of a material. The method comprises the steps of: a) obtaining measurements on the material using a reference point indentation device, wherein the device comprises a probe mating chuck system, and wherein the system comprises a test probe and a magnetic chuck, wherein the test probe has an end proximal to a tip and an end distal to the tip, and wherein the distal end of the test probe has a self-centering mate comprising a countersink of about 90 degrees to about 100 degrees to a depth of between 0.010 in. and 0.035 in., and wherein the self-centering mate is connected to a magnetic chuck comprising an alignment ball, a ring magnet and an impact transfer shaft; b) analyzing the data to provide a measurement of the material property.

DETAILED DESCRIPTION OF THE INVENTION

Figure 1:
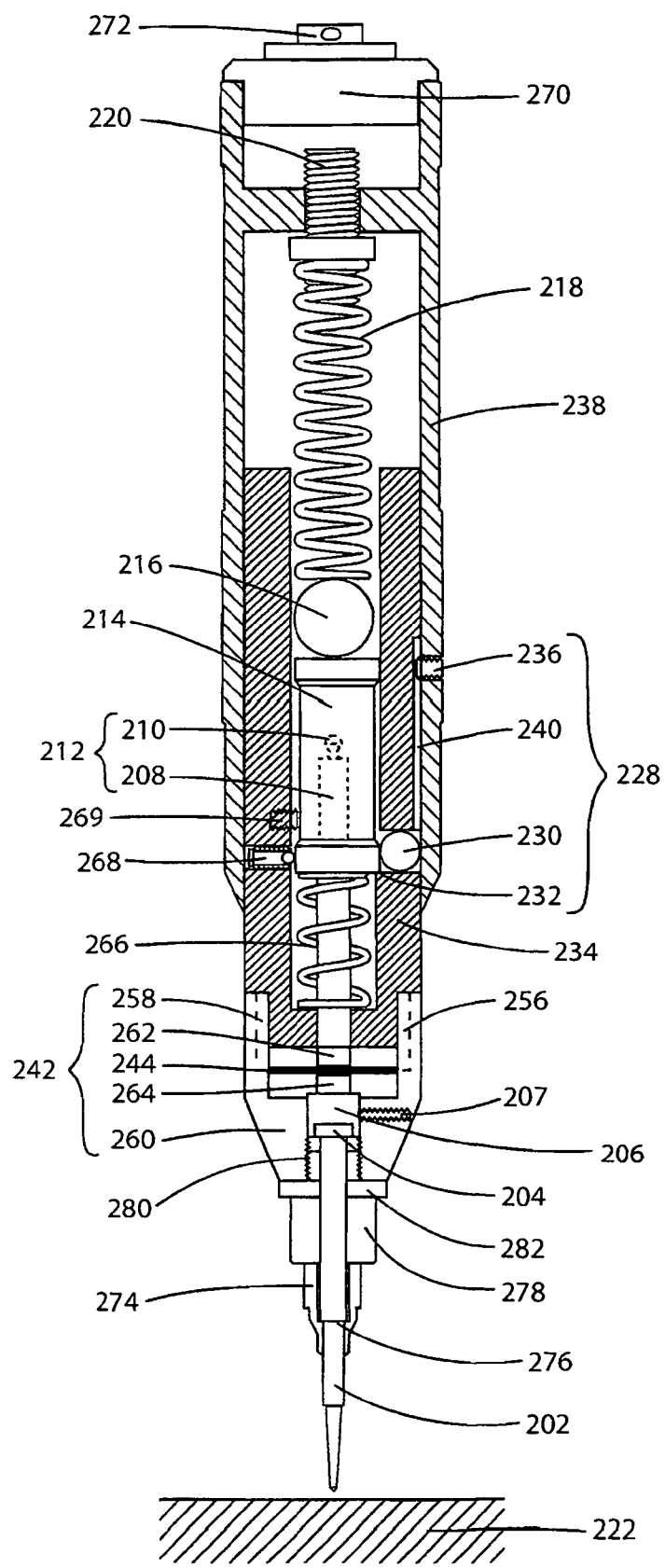
FIG. 1 shows an embodiment of a reference point indentation device as presented in WO 2012/015592.
Figure 2:
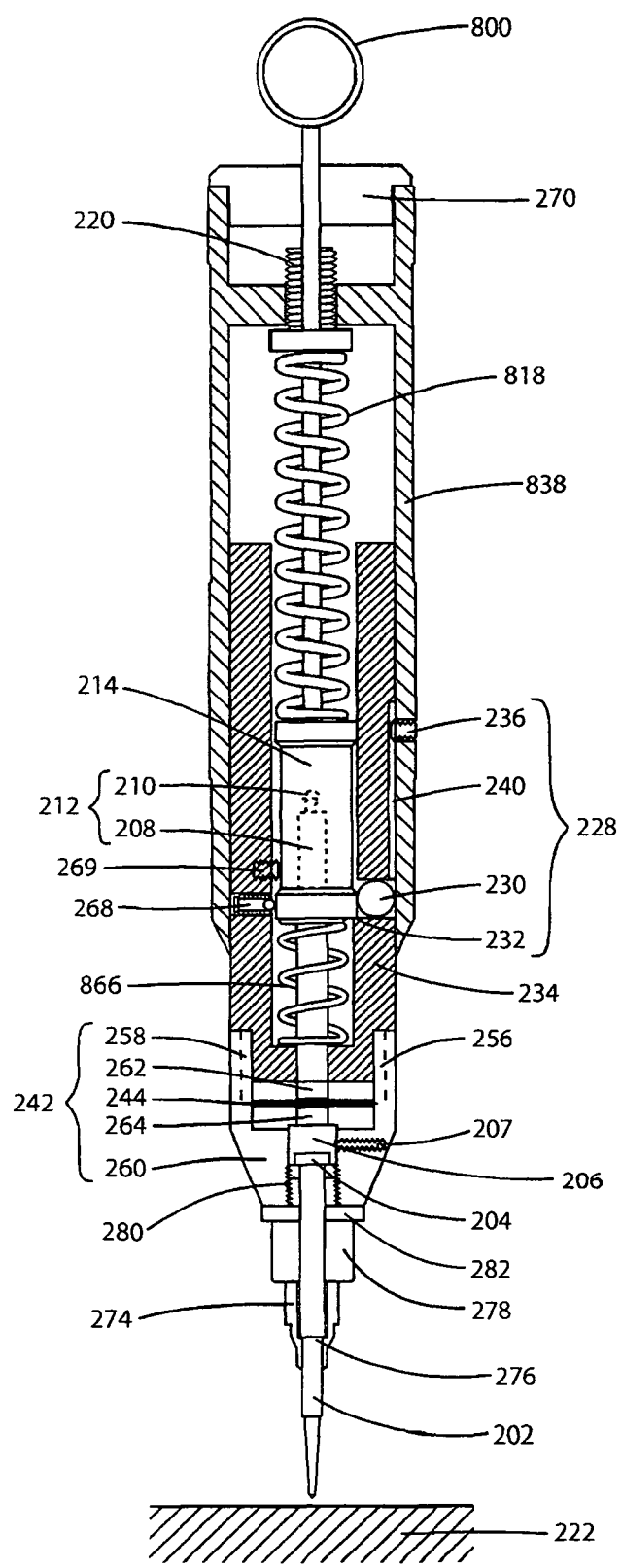
FIG. 2 shows another embodiment of a reference probe indentation device as presented in WO 2012/015592.
Figure 3:
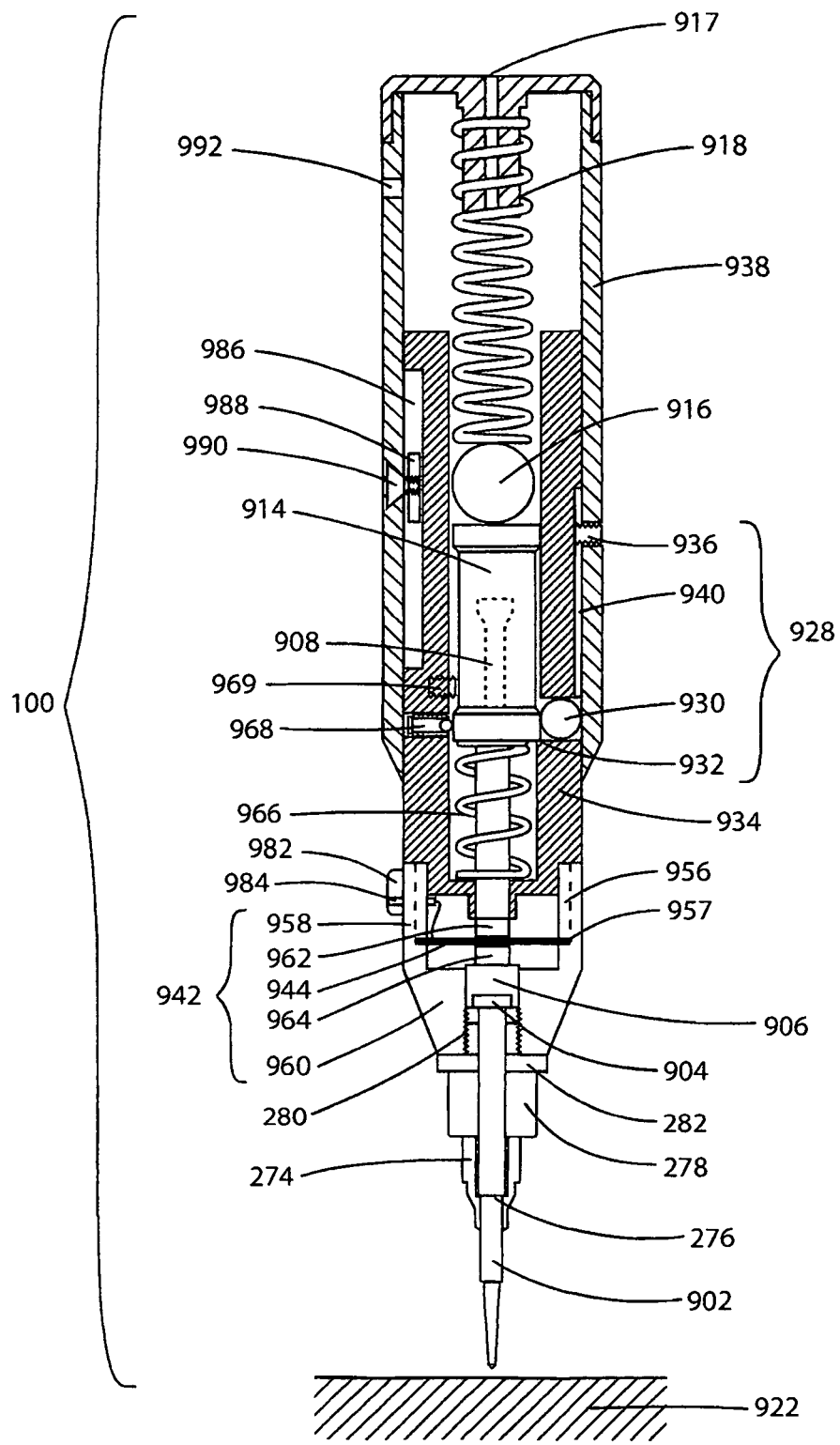
FIG. 3 shows another embodiment of a reference probe indentation device as presented in WO 2012/015592.

The present invention specifically relates to self-aligning probes, related magnetic chucks that mate with the probes, devices using the probes that measure material properties and corresponding methods. For example, WO 2012/015592 describes a method and test probe-based device for reference point indentation without a reference probe. FIGS. 1-3 show embodiments of the WO 2012/015592 reference point indentation device.

FIG. 1 shows a mechanical embodiment of the device described in WO 2012/015592. A test probe 202 is connected to a force generator which is in the form of an impact generator consisting of an optional magnet 204 in a probe holder 206 connected to an impact transfer rod 208 that is terminated by an impact transfer rod adjustment screw 210. Adjustment screw 210 effectively changes the length of the impact transfer assembly 212 consisting of the impact rod 208 and the impact transfer rod attachment screw 210. The impact transfer rod adjustment screw 210 is impacted by an impact mass 214 that is driven by a force normalizing ball 216 driven by a primary spring 218. The impact mass is retained by set screw 269, which prevents the mass from moving upwards when the primary spring 218 is not compressed. The primary spring adjustment screw 220, together with the impact transfer rod adjustment screw 210, adjusts the maximum force applied to the sample 222 during the impact.

The impact is triggered by a trigger device 228 consisting of a trigger ball 230 that pushes the impact mass 214 off a ledge 232 machined into an inner housing 234. The impact mass 214 then impacts the impact transfer assembly 212. The trigger ball 230 is pushed by a set screw 236 held in the outer housing 238. The set screw 236 travels down a groove 240 in the inner housing 234 as the primary spring 218 is compressed by the operator (not shown) applying a force to the outer housing 238. In this regard, the outer housing 238 moves relative to the inner housing 234 thereby building potential energy in the primary spring 218. Upon actuation of a trigger device 228, the potential energy of the primary spring 218 is transferred into kinetic energy whereby the normalizing ball 216 contacts the impact mass 214 which contacts the transfer rod adjustment screw 210.

A measurement device 242 monitors the displacement of the test probe 202 in the sample 220 resulting from an impact. Measurement device 242 can have several embodiments implemented to quantify the indentation measurement. As examples: (1) the measurement device 242 can measure the relative displacement of the test probe 202 with a capacitive sensor, linear variable differential transformer (LVDT), or other electronic displacement sensor; (2) the measurement device 242 can measure the relative displacement of the test probe with a mechanical mechanism such as used in machinist's dial gauges.

After an impact the secondary spring 266 pushes the impact mass 214 back up the inner housing 234. The impact mass is pushed laterally by a ball plunger 268 onto the ledge 232, ready for the next impact (if needed). The end cap 270 can have an optional leveling indicator 272, such as a bubble level, so the operator can monitor the orientation of the device during operation, if desired.

The flexure assembly 244 requires a calibration to convert the output voltage to microns. This requires a custom set up consisting of a calibrated displacement transducer and a voice coil to provide a given displacement. The flexure assembly 244 is displaced by a ramp function generated by the calibration device with known displacements. The output voltage from the flexure assembly 244 is recorded and a linear regression models the relationship between the output voltage of the flexure assembly 244. Alternatively, if measurements are reported as ratios of indentation distances into a reference material relative to indentation distances into the material under test, then the need for absolute measurements is decreased. It is still useful, however, to have a rough idea of absolute measurements to be sure the ratios come from comparable absolute measurements in different instruments.

FIG. 2 illustrates a modified version of the embodiment illustrated in FIG. 1. In this embodiment, a separate device such as a plunger 800 is used to load the primary spring 818. Instead of a force being applied to the outer housing 838 by the operator, the plunger 800 is used to apply the force to the primary spring 818 (e.g., store potential energy in the primary spring 818). The operator would push the plunger 800 inward or distally to load the primary spring 818 where the plunger 800 would lock in place. After the device triggers, either through a separate trigger button or through advancement of the outer housing 838, the plunger 800 would be turned and pulled back to the original position where it could be pushed back in for the next indentation cycle. A secondary spring 866 may assist in restoring the plunger 800 back to the starting or original position.

FIG. 3 shows another embodiment of the probe device presented in WO 2012/015592. The total mass of this embodiment is less than 0.5 lbs making the same lightweight and easy to manipulate and use. It should be understood that the probe device in general may weigh more or less. As seen in FIG. 3, a probe 902 is connected to an impact generator consisting of an optional magnet 904 in a probe holder 906 connected to an impact transfer rod 908. Impact transfer rod 908 is impacted by an impact mass 914 (weighing 0.011 lb) that is driven by a force normalizing ball 916 driven by a primary spring 918 with a spring constant of 1.4 lb/in. The impact mass is retained by set screw 969, which prevents the mass from moving upwards when the primary spring 918 is not compressed. The primary spring 918 is held at the other end by an end cap with a first vent hole 917, which is connected to the outer housing 938. There is a second vent hole 992 located in the side of the outer housing 938. The vent holds 917 and 992 mitigate any contribution of trapped air to the effective spring constant of the primary spring 918.

The impact is triggered by a trigger device consisting of a trigger ball 930 that pushes the impact mass 914 off a ledge 932 machined into the inner housing 934 when the primary spring is compressed to a force of about 11N (typically in the 8N to 12N range). The trigger ball 930 is pushed by a set screw 936 held in the outer housing 938. The set screw 936 travels down a groove 940 located in the inner housing 934 as the primary spring 918 is compressed by the operator (not shown) applying a force to outer housing 938. In this regard, the outer housing 938 moves relative to the inner housing 934 thereby building potential energy in the primary spring 918. A housing alignment guide 988 is retained by a set screw 990 and follows a machined groove 986 in the inner housing 934 to maintain proper alignment when the operator compresses the outer housing 992. This allows for more precision for the trigger device 928. Upon actuation of the trigger device 928, the potential energy (e.g., around 0.17 J) of the primary spring 918 is then transferred into kinetic energy whereby the normalizing ball 916 contacts the impact mass 914 which contacts the impact transfer rod 908.

A measurement device 942 monitors the displacement of the probe 902 in the sample 922 resulting from an impact. The measurement device 942 consists of a flexure assembly 944 consisting of a flexure 246, with a spring constant of 26.1 lb/in, made of hardened Beryllium Copper with strain gauges. The ends of the flexure assembly 944 rest freely in grooves 956 and 958 in the nose cone 960. The center of the flexure assembly has a hole that slips over the impact transfer rod 908 and is held in place by an upper stop 962 and lower stop 964, which limits the travel of the test probe into the sample (travel limited to less than 0.014"). The reference point from which displacements are measured is the ledge 957 on the nose cone 960. The reference mass is 0.34 lb and consists primarily of the nose cone 960 and inner housing 934. Due to the short duration of the impact (less than 1 millisecond) the reference mass stays substantially fixed in time (to within approximately 1 micron), allowing for the displacement to be measured without a physical reference probe in contact with the sample.

After impact, the secondary spring 966, with a spring constant of 1.2 lb/in, pushes the impact mass 914 up the inner housing 934. The impact mass is pushed laterally by a ball plunger 968 onto the ledge 932 and held into place with a 0.5 lb lateral force, ready for the next impact (if needed). The end cap 917 can have an optional leveling indicator, such as a bubble level, so the operator can monitor the orientation of the device during operation, if desired.

Figure 4:
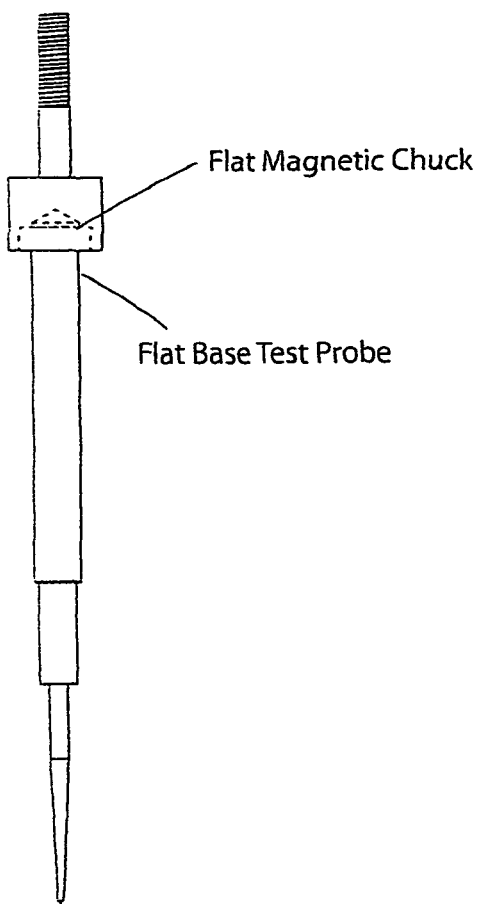
FIG. 4 shows a chuck-probe system as presented in WO 2012/015592.

FIG. 4 shows a probe and mating chuck as presented in WO 2012/015592. Test probe 401 has a flat base in contact with a flat magnetic chuck 403 (listed as optional magnet 204 in FIGS. 1-2 and optional magnet 904 in FIG. 3). The flat magnetic chuck is in a probe holder 405 (e.g., a ring magnet). Impact transfer shaft 407 is connected to probe holder 405.

In certain cases, it was found that the probe and mating chuck system consisting of a flat magnetic chuck and a flat backed test probe (FIG. 4) did not provide for optimal alignment of the test probe 401. Debris can build up on the surface between the flat magnetic chuck and the flat test probe. Where this occurs, measurement errors on the order of 10% can be observed during the evaluation of material properties. The debris build up may also result in magnetic chuck damage due to the transfer of impacts through the brittle magnet material.

Figure 5:
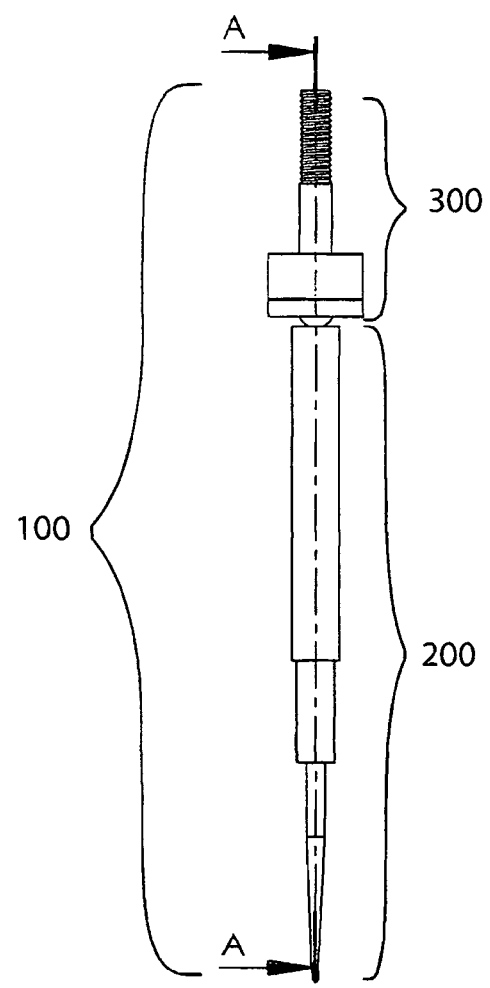
FIG. 5 shows a chuck-probe system according to the present invention.
Figure 6:
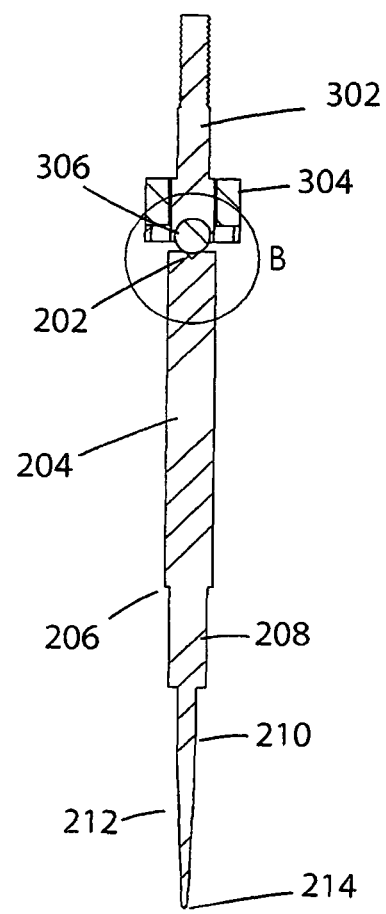
FIG. 6 shows another view of a chuck-probe system according to the present invention.

FIG. 5 shows a self-aligning probe and mating chuck system 100 according to the present invention. Test probe 200 is in contact with magnetic chuck 300. As shown in FIG. 6, test probe 200 consists of a self-centering mate 202, a main body 204, a probe stop 206, a guide portion 208, an extension shaft 210, a tapered shaft 212, and tip 214. The probe stop 206 prevents the probe from being removed during retraction by a guide. The probe design allows for easy penetration of soft tissue without the use of a hypodermic needle to cut through it (e.g., skin).

In an embodiment, the tip 214 of test probe 200 is 90 degrees and conical with a sharp point (typically less than 0.004 in. radius). The conical base of tip 214 typically has a diameter between 0.010 in. and 0.035 in. (e.g., 0.015 in.) with a tight tolerance (e.g., ±0.0005 in.). The diameter is small enough to allow tip 214 to pierce soft materials (e.g., tissue) with a low force, but it is large enough to transfer force generated from a reference point indentation to a test specimen (e.g., bone).

Tapered shaft 212, which is above tip 214, oftentimes has a taper of 1.25 to 3.75 degrees from normal (e.g., 2.5 degrees from normal) to a typical total length of 0.2 in. to 0.6 in. (e.g., 0.4 in.). This allows the probe to support high impact forces (e.g., ~35N to 40N peak force) that are transferred down to the tip and into the sample. Extension shaft 210 is usually not tapered and is typically between 0.1 in. to 0.5 in. in length (e.g., 0.2 in.). The extension shaft 210 can allow for thicker samples (e.g., soft tissue) to be tested without interference from the probe guide.

Test probe 200 can be made of any suitable material or combinations of material. Nonlimiting examples of such materials include: 440C hardened stainless steel; tungsten carbide. Tip 214 may be made of the same material as generally used for probe 200, or it could be a different material such as diamond.

Magnetic chuck 300 (FIG. 6) consists of an impact transfer shaft 302, a ring magnet 304, and an alignment ball 306. Impact transfer shaft 302 transmits energy generated from the reference point indentation device through the alignment ball 306 to test probe 200. During this energy transfer, ring magnet 304 and alignment ball 306 remain securely fixed. Chuck-probe system 100 substantially prevents energy loss and compliance due to debris buildup. It furthermore applies a precision axial load to a sample, minimizing offset forces that would create measurement altering torques. Chuck-probe system additionally substantially lessens, or even prevents, damage to magnet 304.

Figure 7:
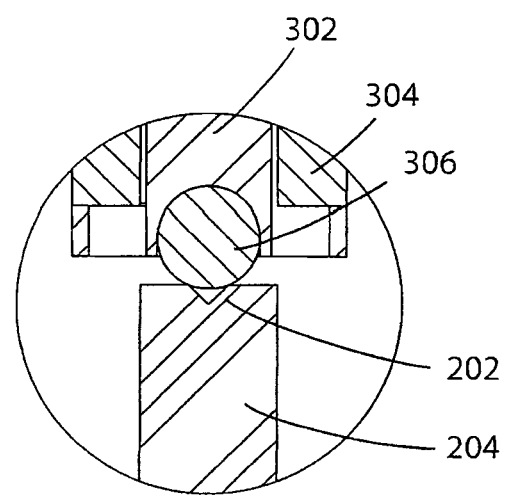
FIG. 7 shows a detailed illustration of the mating surface between test probe 200 and magnetic chuck 300.

FIG. 7 shows a detailed illustration of the mating surface between test probe 200 and magnetic chuck 300. Self-centering mate 202 consists of a 90 degree countersink to a particular depth (e.g., 0.018 in.) centered along the long axis of test probe 200. (Although the shown countersink is 90 degrees, it may vary from just about 90 degrees to about 100 degrees—e.g., about 90 degrees to about 100 degrees, about 90 degrees to about 98 degrees, about 90 degrees to about 96 degrees, about 90 degrees to about 94 degrees, and about 90 degrees to about 92 degrees.) The self-centering mate 202, shown in the cross section mates with alignment ball 306 such that there is contact along a circular profile in which the center is free from contact. Alignment ball 306 ensures magnetic chuck 300 is centered with the long axis of test probe 200. It also transfers energy from the instrument through magnetic chuck 300 to test probe 200 and, eventually, to the sample in a precise manner.

Figure 8:
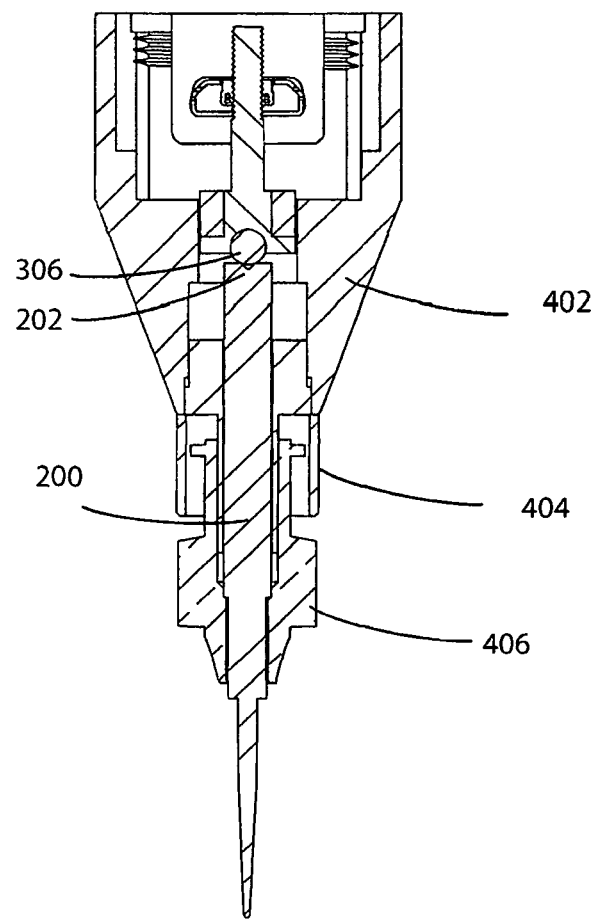
FIG. 8 shows an illustration of chuck-probe system 100 integrated into a reference point indentation device.

FIG. 8 shows an embodiment of a probe and mating chuck system 100 integrated into a reference point indentation device. To implement the system, test probe 200 is inserted into nose cone 402 by hand through a luer lock 404 of the reference point indentation device. Magnetic ball chuck 300 pulls test probe 200 toward alignment ball 306 and centers the test probe. It also pushes any debris aside. An operator (not shown) twists on guide 406, which locks into luer lock 404. Guide 406 is designed to maintain lateral alignment of test probe 200 and prevent inadvertent extraction of the test probe.

When the probe and mating chuck system of the present invention is used in a reference point indentation device without a reference probe as described in WO 2012/015592, the standard deviation of measurements taken on PMMA over 35 test runs is typically at least 5% less than the standard deviation of measurements taken by the device including the chuck probe system discussed in WO 2012/015592 on PMMA over 35 test runs. In certain cases, the obtained standard deviation is at least 7.5%, 10.0%, 20%, 30%, 40% or 50% less.

The probe and mating chuck system of the present invention substantially reduces debris buildup between the chuck and probe as compared to the reference point indentation device as described in WO 2012/015592. In certain cases, it reduces debris buildup by at least 20%. Oftentimes, it decreases debris buildup by at least 30%, 40%, 50%, 60%, 70%, 80% or 90%.

Experimental Results

Self-Centering Mate Geometries

Different geometries of self-centering mate 202 were tested, totaling 10 prototype test probes (200). Countersinks of 90 and 120 degrees at different depths were tested as well as a 3/32 in. ball end groove designed to mate with a 3/32 in. alignment ball 306. Each configuration was tested on a calibration material (PMMA) 30 times, and standard deviations were obtained. Graph A below shows the experimental results.

Magnetic Chuck Configurations

Figure 9:
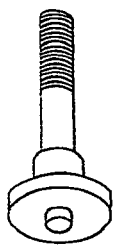
FIG. 9 shows three variations of magnetic chuck configuration.
Figure 9:
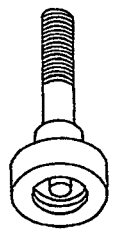
Figure 9:

Three variations of chuck configurations were tested. The first configuration (901 in FIG. 9) is a "flat" magnetic chuck. Configuration 903 is a "flat centering" magnetic chuck, and configuration 905 is a "ball" magnetic chuck configuration of the present invention. Each configuration was tested 35 times and the following standard deviations were obtained: configuration 901, STDEV=1.75; configuration 903, STDEV=2.12; configuration 905, STDEV=1.20.

Probe and Mating Chuck System Standard Deviations and Mean Drift

The probe and mating chuck system of the present invention ("V Probe") was tested against the probe system discussed in WO 2012/015592 ("Flat Probe"). The experiment was conducted in 3 phases: 1) Clean—clean magnetic chuck and clean probe; 2) Dirty 1—pressed end of the probe on a dusty surface; 3) Dirty 2—pressed end of probe on dusty surface again. Each phase consisted of 30 indentations on a calibration material (PMMA) where the probe was reset at an interval of 10 to determine settling effects. The standard deviations for the V-Probe were as follows: Clean (0.97); Dirty 1 (1.06); Dirty 2 (1.35). The standard deviations for the Flat Probe were as follows: Clean (1.13); Dirty 1 (1.25); Dirty 2 (2.23). In addition to reducing the standard deviations, the drift (change in mean measurement over time) is improved with the present invention. For each phase of 30 indentations conducted in this experiment, the probe was removed from the chuck after 10 indentations and reinserted. This was to investigate drift, which is due to debris buildup, resulting in the probe settling differently in the chuck. The difference in means from the first indentation set to the last indentation set on the phase "Dirty 2" was 4.5% for the Flat Probe and only 0.2% for the V-Probe.

The invention claimed is:

1. A self-aligning test probe integrated into a reference point indentation device, wherein the self-aligning test probe has an end proximal to a tip and an end distal to the tip, and wherein the distal end of the test probe has a self-centering mate comprising a countersink of about 90 degrees to about 100 degrees to a depth of between 0.010 in. and 0.035 in., and wherein the self-centering mate is connected to a magnetic chuck comprising an alignment ball, a ring magnet and an impact transfer shaft, and wherein the self-centering mate is included in the main body of the test probe, and wherein the main body of the test probe is connected to a probe stop, and wherein the probe stop is connected to a guide portion, and wherein the guide portion is connected to an extension shaft, and wherein the extension shaft is connected to a tapered shaft which is connected to the tip, and wherein the self-aligning test probe is inserted into a nose cone of the reference point indentation device through a luer lock connected to a guide designed to maintain lateral alignment of the self-aligning test probe.

2. The test probe according to claim 1, wherein the tip of the test probe is 90 degrees and conical, and wherein the tip has a point less than 0.004 in. in radius.

3. The test probe according to claim 2, wherein the test probe mates with the alignment ball such that there is contact along a circular profile with a center, and wherein the center is free from contact.

4. The test probe according to claim 3, wherein the tapered shaft has a taper from 1.25 to 3.75 degrees from normal.

5. The test probe according to claim 4, wherein the tapered shaft has a total length of 0.2 in. to 0.6 in., and wherein the extension shaft is not tapered, and wherein the extension shaft is between 0.1 in. and 0.5 in. in length.

6. A method of measuring a property of a material, wherein the method comprises the steps of:
 a) obtaining measurements on the material using a reference point indentation device, wherein the device comprises a probe mating chuck system, and wherein the system comprises a self-aligning test probe and a magnetic chuck, wherein the self-aligning test probe has an end proximal to a tip and an end distal to the tip, and wherein the distal end of the self-aligning test probe has a self-centering mate comprising a countersink of about 90 degrees to about 100 degrees to a depth of between 0.010 in. and 0.035 in., and wherein the self-centering mate is connected to a magnetic chuck comprising an alignment ball, a ring magnet and an impact transfer shaft, and wherein the self-centering mate is included in the main body of the test probe, and wherein the main body of the test probe is connected to a probe stop, and wherein the probe stop is connected to a guide portion, and wherein the guide portion is connected to an extension shaft, and wherein the extension shaft is connected to a tapered shaft which is connected to the tip, and wherein the self-aligning test probe is inserted into a nose cone of the reference point indentation device through a luer lock connected to a guide designed to maintain lateral alignment of the self-aligning test probe
 b) analyzing the data to provide a measurement of the material property.

7. The method according to claim 6, wherein the tip of the test probe is 90 degrees and conical, and wherein the tip has a point less than 0.004 in. in radius.

8. The method according to claim 7, wherein the test probe mates with the alignment ball such that there is contact along a circular profile with a center, and wherein the center is free from contact.

9. The method according to claim 8, wherein the tapered shaft has a taper from 1.25 to 3.75 degrees from normal.

10. The method according to claim 9, wherein and wherein the tapered shaft has a total length of 0.2 in. to 0.6 in., and wherein the extension shaft is not tapered, and wherein the extension shaft is between 0.1 in. and 0.5 in. in length.

* * * * *